(12) United States Patent
Marfat

(10) Patent No.: US 11,083,711 B2
(45) Date of Patent: Aug. 10, 2021

(54) AMINE PRODRUGS OF PHARMACEUTICAL COMPOUNDS

(71) Applicant: BIOHAVEN THERAPEUTICS LTD., New Haven, CT (US)

(72) Inventor: Anthony Marfat, Mystic, CT (US)

(73) Assignee: Biohaven Therapeutics Ltd., New Haven, CT (US)

( * ) Notice: Subject to any disclaimer, the term of this patent is extended or adjusted under 35 U.S.C. 154(b) by 0 days.

(21) Appl. No.: 16/544,166

(22) Filed: Aug. 19, 2019

(65) Prior Publication Data

US 2019/0365721 A1 Dec. 5, 2019

Related U.S. Application Data

(63) Continuation of application No. 15/775,897, filed as application No. PCT/US2016/062400 on Nov. 17, 2016, now abandoned.

(60) Provisional application No. 62/257,533, filed on Nov. 19, 2015.

(51) Int. Cl.
| | |
|---|---|
| C07D 277/82 | (2006.01) |
| A61K 31/428 | (2006.01) |
| A61K 9/14 | (2006.01) |
| C07D 417/12 | (2006.01) |
| C07F 9/6541 | (2006.01) |
| A61K 47/16 | (2006.01) |

(52) U.S. Cl.
CPC .............. *A61K 31/428* (2013.01); *A61K 9/14* (2013.01); *A61K 47/16* (2013.01); *C07D 277/82* (2013.01); *C07D 417/12* (2013.01); *C07F 9/6541* (2013.01)

(58) Field of Classification Search
CPC .................................................. C07D 277/82
See application file for complete search history.

(56) References Cited

U.S. PATENT DOCUMENTS

| | | |
|---|---|---|
| 2003/0216469 A1 | 11/2003 | Bryans et al. |
| 2004/0176430 A1 | 9/2004 | Sterling et al. |
| 2013/0030359 A1 | 1/2013 | Vetter et al. |
| 2015/0111932 A1 | 4/2015 | Kandula |

FOREIGN PATENT DOCUMENTS

| | | | |
|---|---|---|---|
| WO | 2004-045601 A1 | 6/2004 | |
| WO | 2006-060110 A2 | 6/2006 | |
| WO | 2007-022073 A2 | 2/2007 | |
| WO | 2009-149436 A1 | 12/2009 | |
| WO | 2013-138753 A1 | 9/2013 | |
| WO | WO 2013/167993 A1 * | 11/2013 | ........... C07D 277/60 |
| WO | 2014-011695 A2 | 1/2014 | |

OTHER PUBLICATIONS

Matos et al., European Journal of Medicinal Chemistry, 63 (2013), pp. 151-161. (Year: 2013).*
Salvatore et al. "Efficient Carbamate Synthesis via a Three-Component Coupling of an Amine, CO2, and Alkyl Halides in the Presence of Cs2CO3 and Tetrabutylammonium Iodide" The Journal of Organic Chemistry, 2001, 66, 1035-1037.
Stark et al. "Enzyme-Catalyzed Prodrug Approaches for the Histamine H3-Receptor Agonist (R)-Methylhistamine" Bioorganic and Medicinal Chemistry, 2000, 9, 191-198.
Hale et al. "Phosphorylated Morpholine Acetal Human Neurokinin-1 Receptor Antagonists as Water-Soluble Prodrugs" Journal of Medicinal Chemistry, 2000, 43, 1234-1241.
Alexander et al. "(Acyloxy)alkyl Carbamates as Novel Bioreversible Prodrugs for Amines: Increased Permeation through Biological Membranes" Journal of Medicinal Chemistry, 1988, 31(2), 318-322.
Safadi et al. "Phosphoryloxymethyl Carbamates and Carbonates—Novel Water-Soluble Prodrugs for Amines and Hindered Alcohols" Pharmaceutical Research, 1993, 10(9), 1350-1355.
International Search Report dated Feb. 2, 2017 issued for corresponding application PCT/US2016/062400 (1 page).
Written Opinion dated Feb. 2, 2017 issued for corresponding application PCT/US2016/062400 (6 pages).
International Preliminary Report on Patentability dated May 22, 2018 issued for corresponding application PCT/US2016/062400 (7 pages).
Extended European Search Report dated Oct. 10, 2019 and Written Opinion issued for corresponding application EP 16867091.7 (12 pages).

* cited by examiner

*Primary Examiner* — Laura L Stockton

(57) ABSTRACT

Disclose are amine prodrugs and methods of synthesis thereof. In particular, the amine prodrug comprises a drug molecule and at least one or more prodrug appendage moieties and the method for synthesis the amine prodrug comprises a step of coupling the drug molecule and at least one or more prodrug appendage moieties. Also disclosed are exemplary riluzole prodrugs and methods of synthesis thereof.

4 Claims, No Drawings

AMINE PRODRUGS OF PHARMACEUTICAL COMPOUNDS

CROSS-REFERENCE TO RELATED APPLICATIONS

This application is a continuation of U.S. application Ser. No. 15/775,897 filed May 14, 2018, which is a national stage application under 35 U.S.C. § 371 of international application no. PCT/US16/62400, filed Nov. 17, 2016 which claims the benefit of and priority to U.S. Provisional Application Ser. No. 62/257,533 filed Nov. 19, 2015, the disclosure of all of which applications are herein incorporated by reference in heir entireties.

TECHNICAL FIELD

The present invention relates to amine prodrugs and methods of synthesis thereof. The amine prodrug comprises a drug molecule and at least one or more prodrug appendage moieties. The method of synthesis thereof comprises a step of coupling the drug molecule and at least one or more prodrug appendage moieties.

BACKGROUND

Discovery of novel prodrugs has been an integral part in current pharmaceutical industry. A prodrug is an alternative form of a drug and is used instead to improve absorbed, distributed, metabolized and excreted (ADME) properties of the drug. The prodrug is administered in an inactive or less active form, and is subsequently converted to its active drug through a normal metabolic process, such as hydrolysis or other chemical reactions, in a subject.

Among commercially available prodrug products, amine prodrugs such as Capecitabine (Xeloda), Docarpamine, Prulifloxacin, Gabapentin enacarbil, and Altrofloxacin have been successfully introduced into market. The primary or secondary amine prodrugs have been made substantially and further prodrugs of tertiary amine or quaternary amine have been also made and are being advanced into clinical development as well. (Prodrugs of Amines, Ana L. Simplicio et al, Molecules, 2008, 13 519-547; Prodrugs of Amines, Jeffrey Krise et al, Prodrugs, Challenges and Rewards Part 1 and Part 2, Springer, N.Y., 2007; Drug Synthesis II, presentation by Tapio Nevalainen, University of Eastern Finland, 2012.)

As such, other amine prodrugs are potential candidates for drug development.

SUMMARY OF THE INVENTION

The present invention provides amine prodrug and methods of synthesis thereof.

In one aspect, the present invention provides a prodrug which comprises a drug molecule and at least one or more prodrug appendage moieties. The prodrug may be formed as:

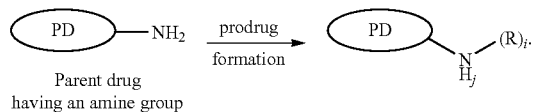

In particular, the prodrug appendage moiety may be coupled to amine of the drug molecule. In this prodrug of the present invention, i may be 1 or 2 and j may be 0 or 1. For example, i is 1 and j is 1; or i is 2 and j is 0.

The prodrug appendage moiety may be independently selected from the group of consisting of:

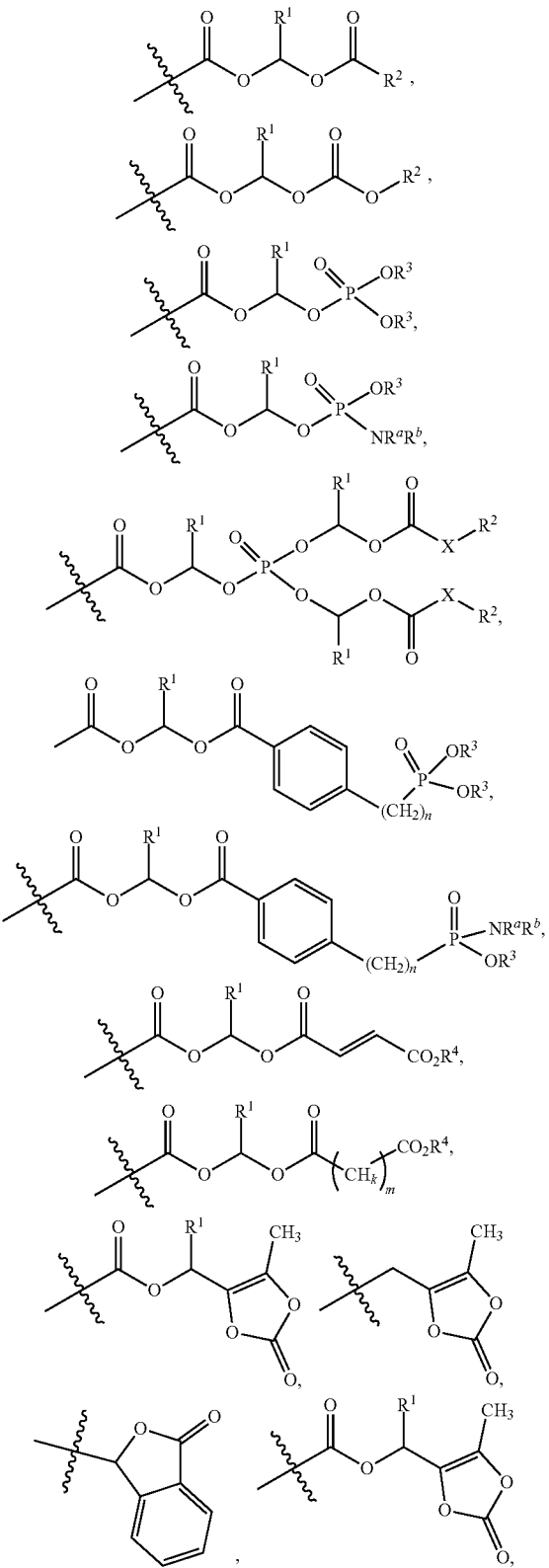

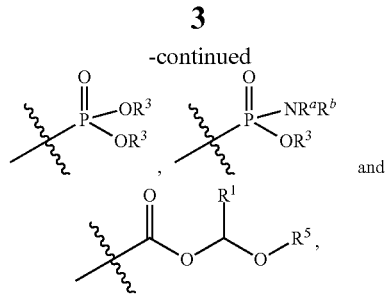

where $R^1$ may be H, alkyl or particularly $C_1$-$C_8$ alkyl;

$R^2$ may be alkyl, cycloalkyl, aryl, or heteroaryl, or halo alkyl, which may be substituted or unsubstituted, $R^3$ may be H, metal, $R^2$ or a substituted or unsubstituted primary, secondary or tertiary amine;

$R^4$ may be H, metal, ammonium salt, or alkyl;

$R^5$ may be a substituted or unsubstituted natural amino acid;

$R^a$ or $R^b$ may be H, alkyl or aryl; or $NR^a$ or $NR^b$ may be an amino acid;

X may be C or O;

k may be 1 or 2, m may be 2-22, or $(CH_k)_m$ may be saturated, unsaturated or conjugated hydrocarbon;

n may be 0-2; and the metal may be Na, K, Li, Ca, Mg, Ag or Zn.

In an exemplary embodiment, and the drug molecule may be riluzole.

In another aspect, the present invention provides a method of preparing a prodrug.

In one embodiment, a method of preparing a riluzole prodrug is provided. The method comprises a step of coupling one or more prodrug appendage moieties to a riluzole molecule as described below.

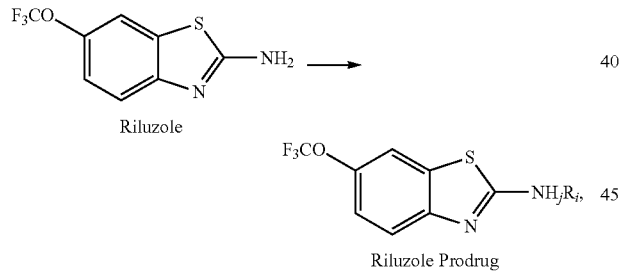

In particular, the prodrug appendage moiety may be coupled to amine of the riluzole molecule where i may be 1 or 2 and j may be 0 or 1. For example, i is 1 and j is 1; or i is 2 and j is 0.

The prodrug appendage moiety may be independently selected from the group of consisting of:

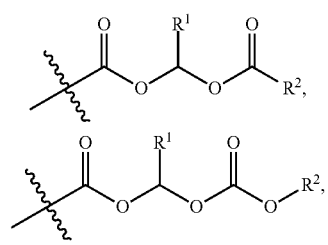

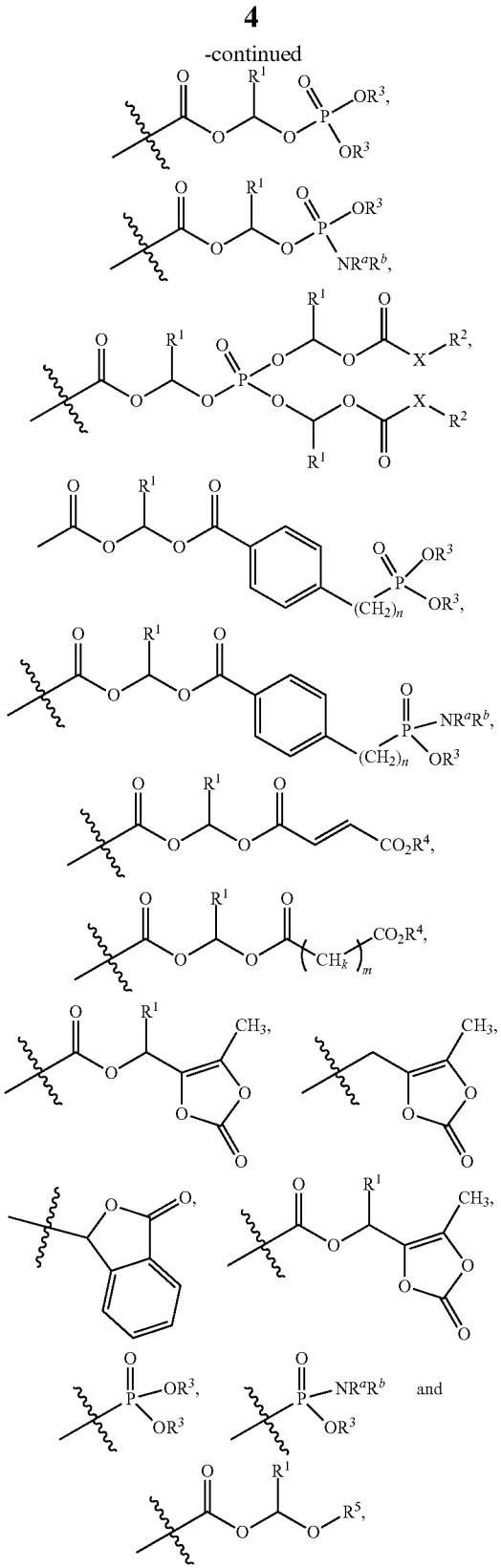

where $R^1$ may be H, alkyl or particularly $C_1$-$C_8$ alkyl; $R^2$ may be alkyl, cycloalkyl, aryl, or heteroaryl, or halo alkyl, which may be substituted or unsubstituted, $R^3$ may be H, metal, $R^2$ or a substituted or unsubstituted primary, secondary or tertiary amine;

$R^4$ may be H, metal, ammonium salt, or alkyl;

$R^5$ may be a substituted or unsubstituted natural amino acid;

$R_a$ or $R_b$ may be H, alkyl or aryl; or $NR^a$ or $NR^b$ may be an amino acid;

X may be C or O;

k may be 1 or 2, m may be 2-22, or $(CH_k)_m$ may be saturated, unsaturated or conjugated hydrocarbon;

n may be 0-2; and the metal may be Na, K, Li, Ca, Mg, Ag or Zn.

Exemplary riluzole prodrug may be:

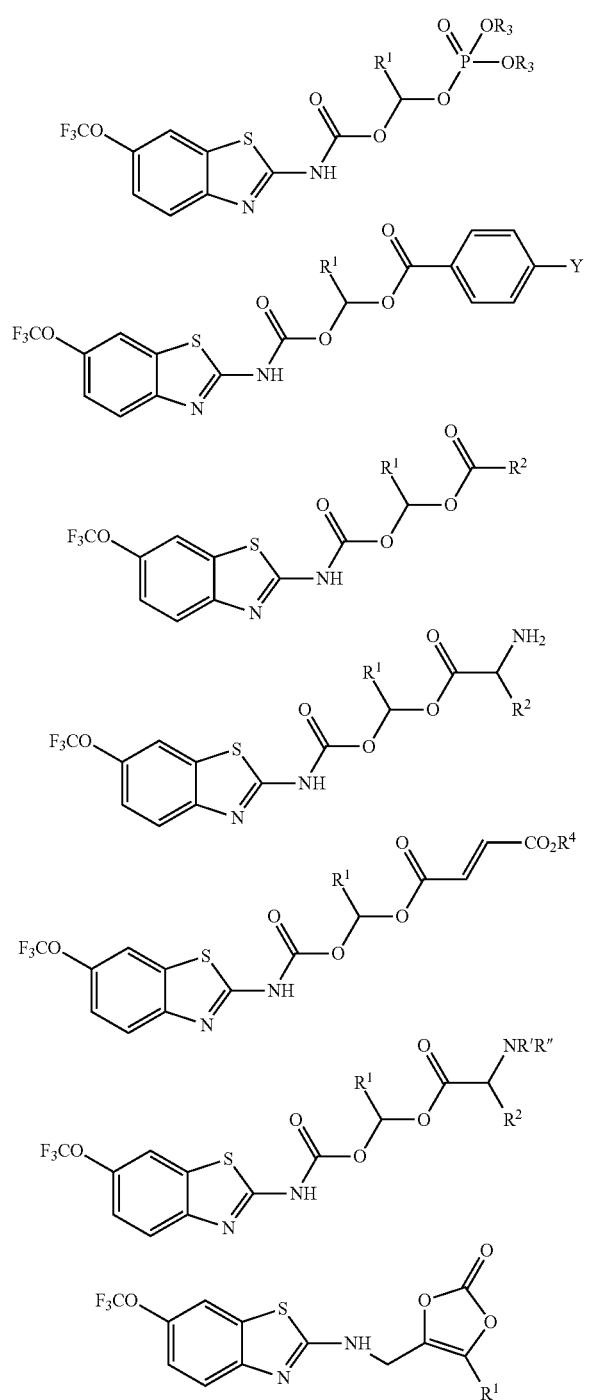

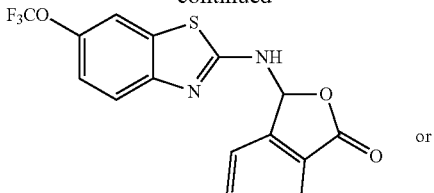

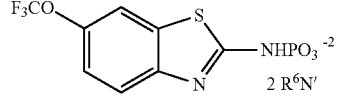

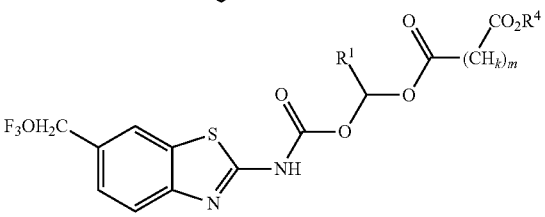

where $R^1$ may be H, alkyl or particularly $C_1$-$C_8$ alkyl; $R^2$ may be alkyl, cycloalkyl, aryl, or heteroaryl, or halo alkyl, which may be substituted or unsubstituted; $R^3$ may be H, metal, $R^2$ or a substituted or unsubstituted primary, secondary or tertiary amine; $R^4$ may be H, metal, ammonium salt, or alkyl; $R^6$ may be alkyl, cycloalkyl, aryl, or heteroaryl, or halo alkyl; N' may be a primary, secondary and tertiary amine which may be substituted or unsubstituted, or metal salts; and Y may be $PO_3H$, $CH_2PO_2H$ or salt thereof. In particular, the metal may be Na, K, Li, Ca, Mg, Ag or Zn.

The present invention also provides a method of synthesizing a riluzole prodrug.

In one embodiment, the method comprises a step of reacting riluzole with

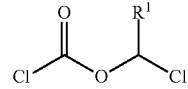

to produce

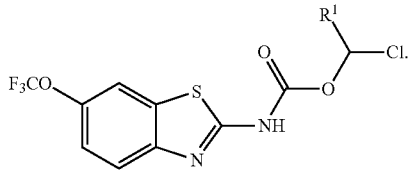

The method further comprises a step of reacting

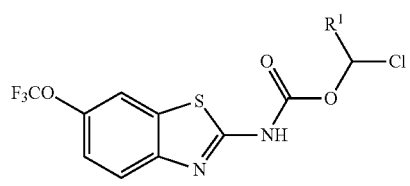

with a compound selected from the group consisting of:

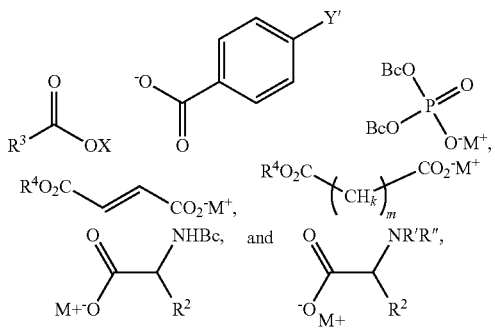

where $R^1$ may be H, alkyl or particularly $C_1$-$C_8$ alkyl;

$R^2$ may be alkyl, cycloalkyl, aryl, or heteroaryl, or halo alkyl, which may be substituted or unsubstituted;

$R^4$ may be H, metal, ammonium salt, or alkyl;

k may be 1 or 2, m may be 2-22, or $(CH_k)_m$ may be saturated, unsaturated or conjugated hydrocarbon;

Bc may be a protecting group;

Y' may be H, $PO_3Bc_2$, $CH_2PO_2Bc$, $MPO_3Bc$ or salt thereof, or $N(R_a)_4^+$, where Ra is H or alkyl;

M may be a metal such as Na, K, Li, Ca, Mg, Ag or Zn; and

R' or R" may be cyclic or acyclic alkyl.

In one embodiment, the method of synthesizing a riluzole prodrug comprises a step of reacting a riluzole, with $CO_2$, $Cs_2CO_3$ and reacting the resulting compound with

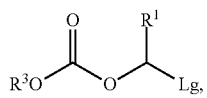

wherein Lg is a leaving group.

In one embodiment, the method of synthesizing a riluzole prodrug comprises a step of reacting a riluzole with

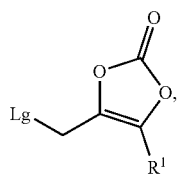

wherein Lg is a leaving group and where $R^1$ may be H, or $C_1$-$C_8$ alkyl.

In one embodiment, the method of synthesizing a riluzole prodrug comprises a step of reacting a riluzole with

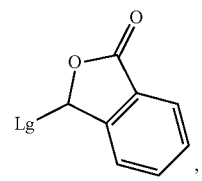

wherein Lg is a leaving group.

In one embodiment, the method of synthesizing a riluzole prodrug comprises a step of reacting riluzole with

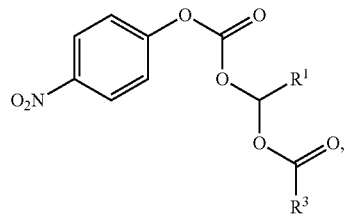

wherein $R^1$ may be H, alkyl or particularly $C_1$-$C_8$ alkyl;

$R^2$ may be alkyl, cycloalkyl, aryl, or heteroaryl, or halo alkyl, which may be substituted or unsubstituted; and $R^3$ may be H, metal, $R^2$ or a substituted or unsubstituted primary, secondary or tertiary amine.

In one embodiment, the method of synthesizing a riluzole prodrug comprises a step of reacting riluzole with $((PhCH_2O)_2PO)_2O$ and sodium bis(trimethylsilyl)amide (NaHMDS) and subsequently reacting the resulting compound with hydrogen:

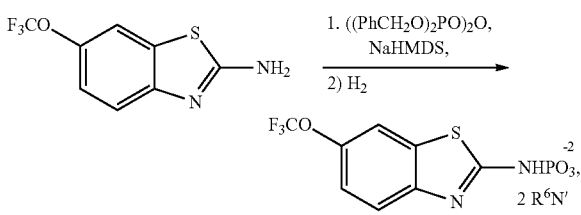

where $R^6$ may be alkyl, cycloalkyl, aryl, or heteroaryl, or halo alkyl; and N' may be a primary, secondary and tertiary amine which may be substituted or unsubstituted, or metal salts.

Other aspects of the invention are disclosed infra.

DETAILED DESCRIPTION OF THE INVENTION

The following is a detailed description provided to aid those skilled in the art in practicing the present invention. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description is for describing particular embodiments only and is not intended to be limiting. All publications, patent applications, patents, figures and other references mentioned herein are expressly incorporated by reference in their entirety.

The following terms are used to describe the present invention. In instances where a term is not specifically defined herein, that term is given an art-recognized meaning by those of ordinary skill applying that term in context to its use in describing the present invention.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or"). Singular word forms are intended to include plural word forms and are likewise used herein interchangeably where appropriate and fall within each meaning, unless expressly stated otherwise.

The term "prodrug" as used herein, is a precursor of a drug which may be administered in an altered or less active form. The prodrug may be converted into the active drug form in physiological environments by hydrolysis or other metabolic pathways. The prodrug may provide improved physiochemical or physiological characteristics to enhance therapeutic effects of the drug.

The term "prodrug appendage moiety" as used herein, refers to a chemical group or moiety covalently or non-covalently attached to a drug molecule, thereby produce a prodrug form of the drug. The prodrug appendage moiety may not alter pharmacokinetic core or properties of the drug molecules by intramolecular rearrangement or cleavage. In certain embodiments, multiple prodrug appendage moieties may be attached to the drug molecule, without limitation. In addition, the prodrug appendage moiety may couple one or more of the drug molecules, without limitation.

The term "riluzole", as used herein, refers to a drug, 6-(trifluoromethoxy)benzothiazol-2-amine, which is generally used to treat amyotrophic lateral sclerosis (ALS). It is also available in the market as RILUTEK®.

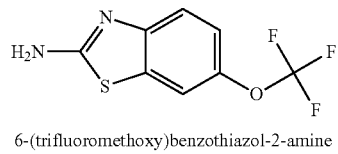

6-(trifluoromethoxy)benzothiazol-2-amine

As used herein, the term "leaving group," or "LG", as used herein, refers to any group that leaves in the course of a chemical reaction involving the group and includes but is not limited to halogen, brosylate, mesylate, tosylate, triflate, p-nitrobenzoate, phosphonate groups, for example.

As used herein, the term "alkyl" refers to a straight-chained or branched hydrocarbon group containing 1 to 18 (e.g., $C_1$—$C_{18}$, inclusive; and any sub-range thereof) carbon atoms. The term "lower alkyl" refers to a $C_1$-$C_6$ alkyl chain. Examples of alkyl groups include methyl, ethyl, n-propyl, isopropyl, n-butyl, sec-butyl, tert-butyl, pentyl (n-, sec-, tert-), and pivaloyl. Alkyl groups may be optionally substituted with one or more substituents.

The term "cycloalkyl" denotes a non-aromatic mono or multicyclic ring system of 3 to 12 carbon atoms such as cyclopropyl, cyclobutyl, cyclopentyl, cyclohexyl and examples of multicyclic cycloalkyl groups include perhydronapththyl, adamantyl and norbomyl groups bridged cyclic group or spirobicyclic groups e.g spiro(4,4)non-2-yl.

As used herein, the term "halogen" or "halide" means —F, —Cl, —Br or —I.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, difluoromethyl, bromomethyl, 1,2-dichloroethyl, 4-iodobutyl, 2-fluoropentyl, and the like. The term "perhaloalkyl" refers to a alkyl group in which all hydrogen atoms are replaced by a halo group (e.g., trifluoromethyl, pentafluoroethyl). In certain embodiments, the haloalkyl may be an activated alkyl.

The term "cycloalkyl" refers to a hydrocarbon 3-8 membered monocyclic or 7-14 membered bicyclic ring system having at least one non-aromatic ring. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, and cyclodecyl.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic monocyclic, bicyclic, or tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, cyclyl, heterocycloalkyl, or heterocyclyl group) is replaced with any desired group that does not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cyclyl, heterocyclyl, wherein alkyl, alkenyl, alkyloxy, aryl, heteroaryl, cyclyl, and heterocyclyl are optionally substituted with alkyl, aryl, heteroaryl, halogen, hydroxyl, amino, mercapto, cyano, nitro, oxo (=O), thioxo (=S), or imino (=NR), wherein R is as defined herein. The substituents on any group (such as, for example, alkyl, alkenyl, alkynyl, aryl, arylalkyl, heteroaryl, heteroaralkyl, cycloalkyl, cycloalkenyl, heterocycloalkyl, and heterocycloalkenyl) can be at any atom of that group, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocycloalkenyl, heterocycloalkyl, arylalkyl, heteroarylalkyl, aryl, heteroaryl, halogen, haloalkyl, cyano, nitro, alkoxy, aryloxy, hydroxyl, hydroxyalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents on alkyl, alkenyl, alkynyl, aryl, aralkyl, heteroaryl, heteroaralkyl, cycloalkyl, cyclyl, heterocycloalkyl, and heterocyclyl include, without limitation halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, (=O), (=S), (=$NR^{15}$), $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)H$, $C(O)R^{17}$, $NR^{15}C(O)R^{17}$, $Si(R^{15})_3$, $OSi(R^{15})_3$, $Si(OH)_2R^{15}$, $P(O)(OR^{15})_2$, $S(O)R^{17}$, or $S(O)_2R^{17}$. Each $R^{15}$ is independently hydrogen, $C_1$-$C_6$ alkyl optionally substituted with cycloalkyl, aryl, heterocyclyl, aryl, or heteroaryl. Each leis independently hydrogen, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl aryl, or heteroaryl. Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $C_3$-$C_6$ cycloalkyl, aryl, heterocyclyl, heteroaryl and $C_1$-$C_4$ alkyl in each $R^{15}$, $R^{16}$ and $R^{17}$ can optionally be substituted with halogen, CN, $C_1$-$C_4$ alkyl, OH, $C_1$-$C_4$ alkoxy, COOH, $C(O)OC_1$-$C_4$ alkyl, $NH_2$, $C_1$-$C_4$ alkylamino, or $C_1$-$C_4$ dialkylamino.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The compounds disclosed in the present invention are available from commercial sources or may be synthesized using reagents and techniques known in the art, including those delineated herein. The chemicals used in the synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Prodrug Appendage Moiety

In one aspect, a novel design of amine prodrugs is provided in the current invention. In particular, the prodrugs may include a parent drug molecule having at least one amine group and at least one prodrug appendage moiety attached to an amine of the parent drug molecule.

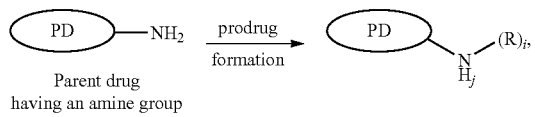

Parent drug having an amine group where R is a prodrug appendage moiety where i may be 1 or 2 and j may be 0 or 1. For example, i is 1 and j is 1; or i is 2 and j is 0.

In certain exemplary embodiment, R is

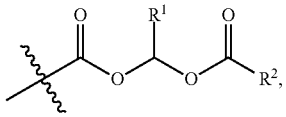

where $R^1$ may be H, alkyl or particularly $C_1$-$C_8$ alkyl; $R^2$ may be alkyl, cycloalkyl, aryl, or heteroaryl, or halo alkyl, which may be substituted or unsubstituted.

In certain exemplary embodiments, R is

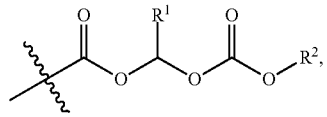

where $R^1$ may be H, alkyl or particularly $C_1$-$C_8$ alkyl; and $R^2$ may be alkyl, cycloalkyl, aryl, or heteroaryl, or halo alkyl, which may be substituted or unsubstituted.

In certain exemplary embodiments, R is

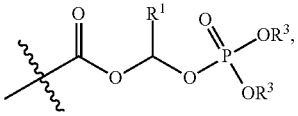

where $R^1$ may be H, alkyl or particularly $C_1$-$C_8$ is alkyl; $R^2$ may be alkyl, cycloalkyl, aryl, or heteroaryl, or halo alkyl, which may be substituted or unsubstituted; and $R^3$ may be H, metal, $R^2$ or a substituted or unsubstituted primary, secondary or tertiary amine. The metal may be Na, K, Li, Ca, Mg, Ag or Zn.

In certain exemplary embodiments, R is

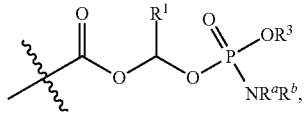

where $R^1$ may be H, alkyl or particularly $C_1$-$C_8$ alkyl; $R^2$ may be alkyl, cycloalkyl, aryl, or heteroaryl, or halo alkyl, which may be substituted or unsubstituted; and $R^3$ may be H, metal, $R^2$ or a substituted or unsubstituted primary, secondary or tertiary amine; and $R^a$ or $R^b$ may be H, alkyl or aryl, or $NR^a$ or $NR^b$ may be an amino acid. The metal may be Na, K, Li, Ca, Mg, Ag or Zn. Aryl, or $NR^a$ or $NR^b$ may be an amino acid. The metal may be Na, K, Li, Ca, Mg, Ag or Zn.

In certain exemplary embodiments, R is

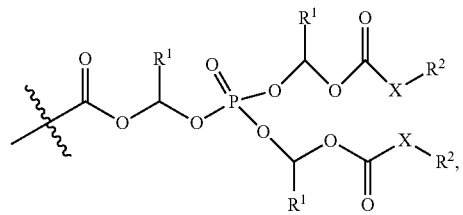

where $R^1$ may be H, alkyl or particularly $C_1$-$C_8$ alkyl; $R^2$ may be alkyl, cycloalkyl, aryl, or heteroaryl, or halo alkyl, which may be substituted or unsubstituted; and X is C or O.

In certain exemplary embodiments, R is

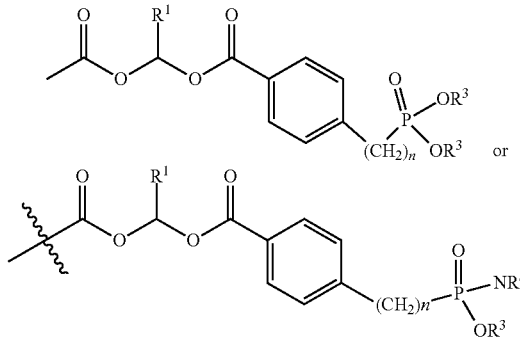

where $R^1$ may be H, alkyl or particularly $C_1$-$C_8$ alkyl; $R^2$ may be alkyl, cycloalkyl, aryl, or heteroaryl, or halo alkyl, which may be substituted or unsubstituted; and $R^3$ may be H, metal, $R^2$ or a substituted or unsubstituted primary, secondary or tertiary amine; and $R^a$ or $R^b$ may be H, alkyl or aryl, or $NR^a$ or $NR^b$ may be an amino acid. n may be 0-2.

In certain exemplary embodiments, R is

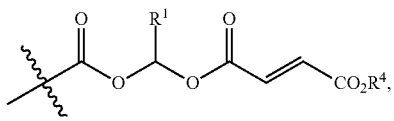

where $R^1$ may be H, alkyl or particularly $C_1$-$C_8$ alkyl; and $R^4$ may be H, metal, ammonium salt, or alkyl;

In particular, the metal may be Na, K, Li, Ca, Mg, Ag or Zn.

In certain exemplary embodiments, R is,

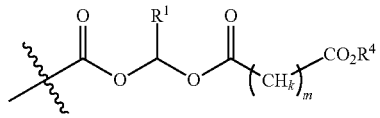

where $R^1$ may be H, alkyl or particularly $C_1$-$C_8$ alkyl; and $R^4$ may be H, metal, ammonium salt, or alkyl; k may be 1 or 2, m may be 2-22, or $(CH_k)_m$ may be saturated, unsaturated or conjugated hydrocarbon. In particular, the metal may be Na, K, Li, Ca, Mg, Ag or Zn.

In certain exemplary embodiments, R is

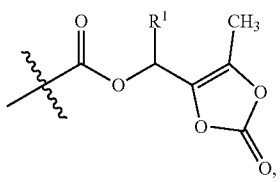

where $R^1$ may be H, alkyl or particularly $C_1$-$C_8$ alkyl.

In certain exemplary embodiments, R is

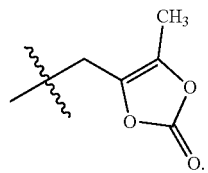 [SMILES: *Cc1oc(=O)oc1C]

In certain exemplary embodiments, R is

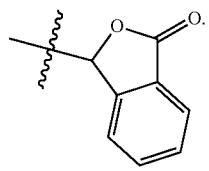 [SMILES: *C1OC(=O)c2ccccc21]

In certain exemplary embodiments, R is

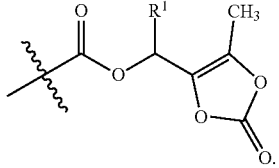

In certain exemplary embodiments, R is

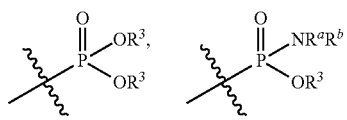

where $R^3$ may be H, metal, alkyl, cycloalkyl, aryl, or heteroaryl, or halo alkyl, which may be substituted or unsubstituted, or a substituted or unsubstituted primary, secondary or tertiary amine; $R^a$ or $R^b$ may be H, alkyl or aryl, or $NR^a$ or $NR^b$ may be an amino acid.

In certain exemplary embodiments, R is

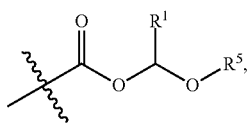

where $R^1$ may be H, alkyl or particularly $C_1$-$C_8$ alkyl; and $R^5$ may be a substituted or unsubstituted natural amino acid;

In certain embodiment, i is 1 and j is 1.

In certain embodiment, i is 2 and j is 0.

In an exemplary embodiment, the amine prodrug may be N-acyloxy carbamate prodrug formed as below,

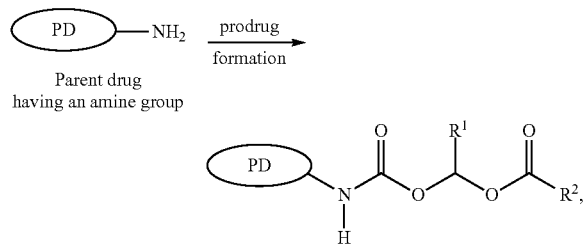

where $R^1$ is be H or $CH_3$; $R^2$ is alkyl, cycloalkyl, aryl, or heteroaryl, or halo alkyl, which may be substituted or unsubstituted.

In certain exemplary embodiments, when the amine of the prodrug is a primary or secondary amine, the N-acyloxy carbamate prodrug itself may further be converted into an N-acyl compound spontaneously by intramolecular O to N acyl migration. As shown Scheme A, the N-acyl compound may be released as consequence and may substantially provide a stable carbamate compound.

Scheme A

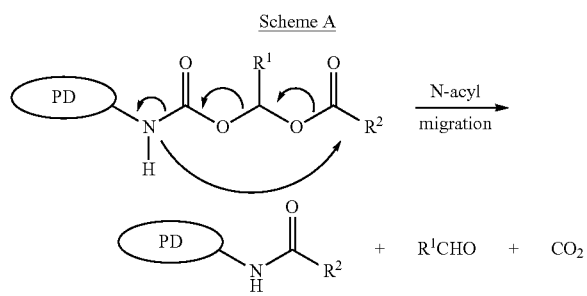

In certain exemplary embodiments, the amine prodrugs may have improved physiochemical stability, thereby providing advantages in isolation, crystallinity, solid state stability, solubility, formulation and the like.

In certain exemplary embodiments, the amine prodrugs may have improved physiological stability when the prodrugs are taken and ingested by the subject. For example, the N-acyloxy carbamate drugs may be converted or released into the drug form more efficiently in the subject without adverse effect.

In certain exemplary embodiments, the amine prodrugs of the invention may have specificity to a certain enzymatic reaction. In yet certain embodiments, the prodrugs may be under metabolic pathway to release the active drug by enzymatic or biochemical reaction.

In certain embodiments, the amine prodrugs of the invention may provide improved cell permeability to a target cell.

In certain embodiments, the appendage moiety of the amine prodrug may provide improved physiochemical stability, improved physiological stability, or specificity to particular enzymes.

Riluzole Prodrugs

In one aspect, the current invention provides riluzole prodrugs. The riluzole prodrug may include a riluzole and at least one or more of prodrug appendage moieties attached to an amine of the riluzole at its aromatic amine.

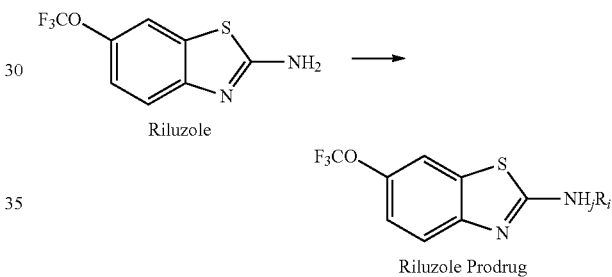

In one embodiment, the riluzole may be coupled to one or more of prodrug appendage moieties (R) to form riluzole prodrugs. In certain embodiments, i is 1 or 2 and j is 0 or 1. For example, i is 1 and j is 1; or i is 2 and j is 0.

In certain exemplary embodiment, R is

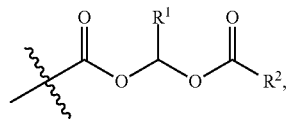

where $R^1$ is H, alkyl or particularly $C_1$-$C_8$ alkyl; $R^2$ is alkyl, cycloalkyl, aryl, or heteroaryl, or halo alkyl, which may be substituted or unsubstituted.

In certain exemplary embodiments, R is

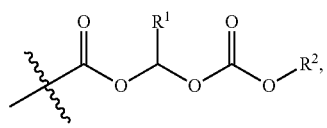

where $R^1$ is H, alkyl or particularly $C_1$-$C_8$ alkyl; and $R^2$ is alkyl, cycloalkyl, aryl, or heteroaryl, or halo alkyl, which may be substituted or unsubstituted.

In certain exemplary embodiments, R is

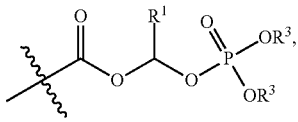

where $R^1$ is H, alkyl or particularly $C_1$-$C_8$ alkyl; $R^2$ is alkyl, cycloalkyl, aryl, or heteroaryl, or halo alkyl, which may be substituted or unsubstituted; and $R^3$ is H, metal, $R^2$ or a substituted or unsubstituted primary, secondary or tertiary amine.

In certain exemplary embodiments, R is

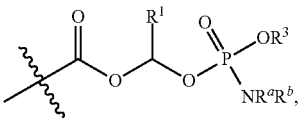

where $R^1$ is H, alkyl or particularly $C_1$-$C_8$ alkyl; $R^2$ is alkyl, cycloalkyl, aryl, or heteroaryl, or halo alkyl, which may be substituted or unsubstituted; $R^3$ is H, metal, $R^2$ or a substituted or unsubstituted primary, secondary or tertiary amine; and $R^a$ or $R^b$ is H, alkyl or aryl or $NR^a$ or $NR^b$ is an amino acid.

In certain exemplary embodiments, R is

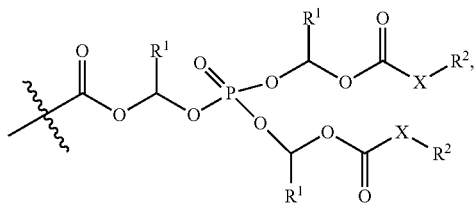

where $R^1$ is H, alkyl or particularly $C_1$-$C_8$ alkyl; $R^2$ is alkyl, cycloalkyl, aryl, or heteroaryl, or halo alkyl, which may be substituted or unsubstituted; and X is C or O.

In certain exemplary embodiments, R is

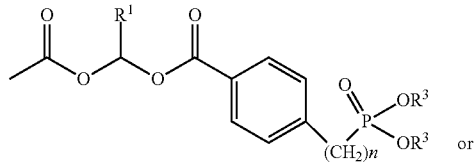

or

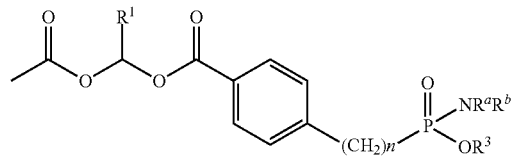

where $R^1$ is H, alkyl or particularly $C_1$-$C_8$ alkyl; $R^2$ is alkyl, cycloalkyl, aryl, or heteroaryl, or halo alkyl, which may be substituted or unsubstituted; $R^3$ is H, metal, $R^2$ or a substituted or unsubstituted primary, secondary or tertiary amine; and $R^a$ or $R^b$ is H, alkyl or aryl or $NR^a$ or $NR^b$ is an amino acid.

In certain exemplary embodiments, R is

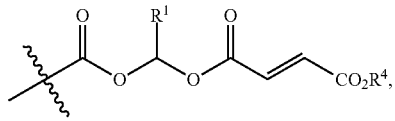

where $R^1$ is H, alkyl or particularly $C_1$-$C_8$ alkyl; and $R^4$ is H, metal, ammonium salt, or alkyl. In particular, the metal is Na, K, Li, Ca, Mg, Ag or Zn.

In certain exemplary embodiments, R is,

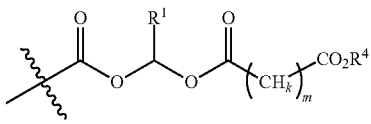

where $R^1$ is H, alkyl or particularly $C_1$-$C_8$ alkyl; $R^4$ is H, metal, ammonium salt, or alkyl; k is 1 or 2, m is 2-22 or $(CH_k)_m$ is saturated, unsaturated or conjugated hydrocarbon. In particular, the metal is Na, K, Li, Ca, Mg, Ag or Zn.

In certain exemplary embodiments, R is

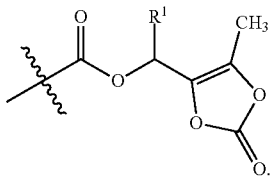

where $R^1$ is H, alkyl or particularly $C_1$-$C_8$ alkyl.

In certain exemplary embodiments, R is

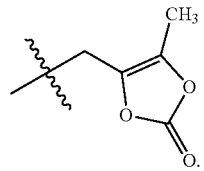 [SMILES: *Cc1oc(=O)oc1C]

In certain exemplary embodiments, R is

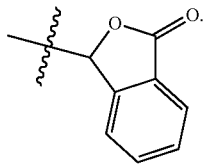

In certain exemplary embodiments, R is

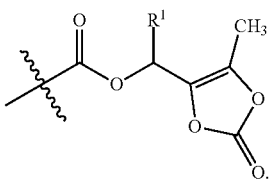

In certain exemplary embodiments, R is

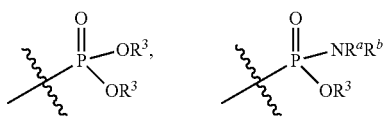

where $R^3$ is H, metal, alkyl, cycloalkyl, aryl, or heteroaryl, or halo alkyl, which may be substituted or unsubstituted, or a substituted or unsubstituted primary, secondary or tertiary amine; $R^a$ or $R^b$ is H, alkyl, aryl or $NR^a$ or $NR^b$ may be an amino acid.

In certain exemplary embodiments, R is

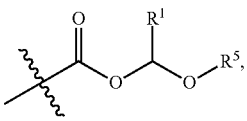

where $R^1$ is H, alkyl or particularly $C_1$-$C_8$ alkyl; and $R^5$ is a substituted or unsubstituted natural amino acid.

In certain embodiment, i is 1 and j is 1.
In certain embodiment, i is 2 and j is 0.
Exemplary riluzole prodrug may be, but not limited to,

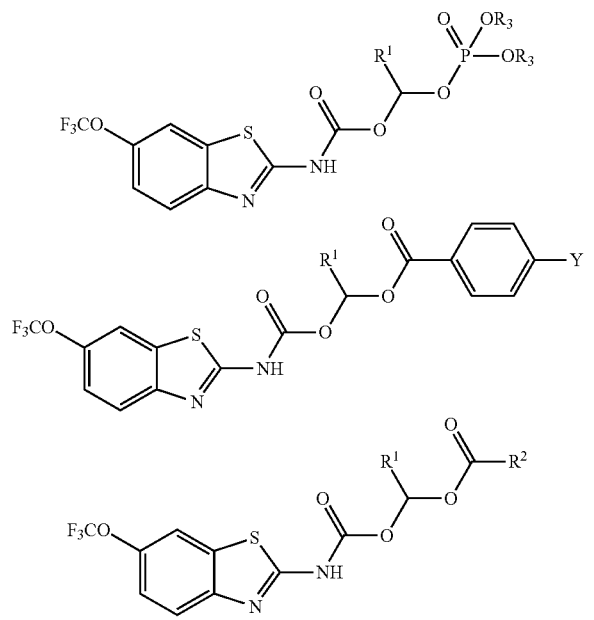

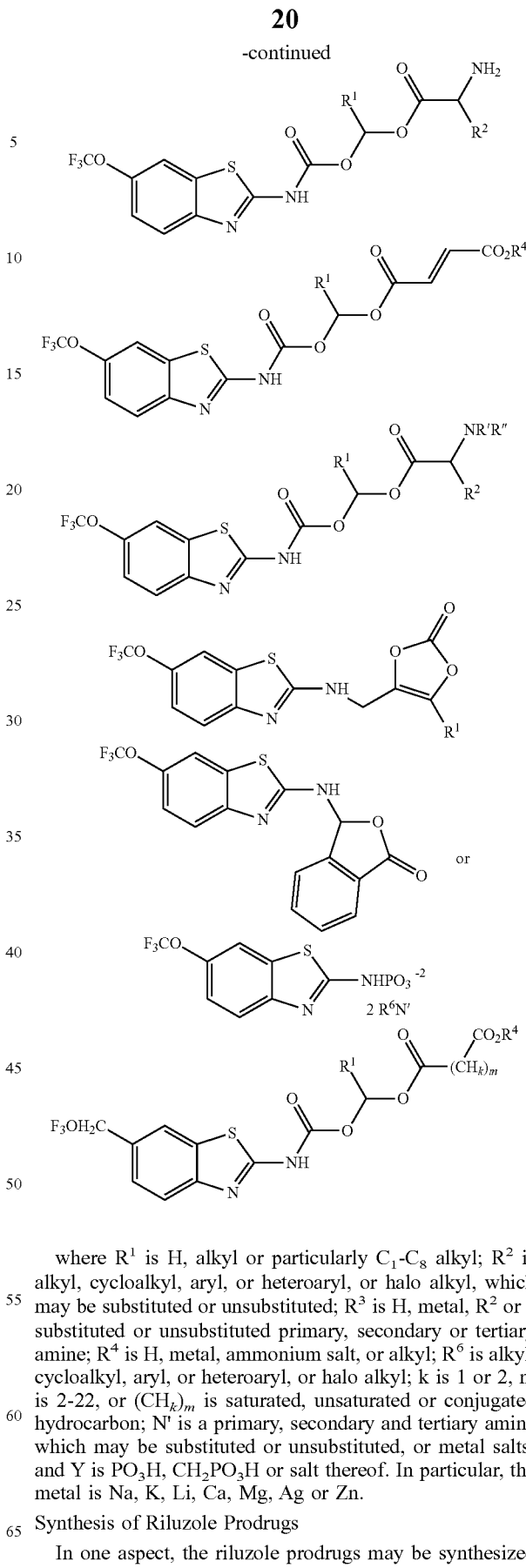

where $R^1$ is H, alkyl or particularly $C_1$-$C_8$ alkyl; $R^2$ is alkyl, cycloalkyl, aryl, or heteroaryl, or halo alkyl, which may be substituted or unsubstituted; $R^3$ is H, metal, $R^2$ or a substituted or unsubstituted primary, secondary or tertiary amine; $R^4$ is H, metal, ammonium salt, or alkyl; $R^6$ is alkyl, cycloalkyl, aryl, or heteroaryl, or halo alkyl; k is 1 or 2, m is 2-22, or $(CH_k)_m$ is saturated, unsaturated or conjugated hydrocarbon; N' is a primary, secondary and tertiary amine which may be substituted or unsubstituted, or metal salts; and Y is $PO_3H$, $CH_2PO_3H$ or salt thereof. In particular, the metal is Na, K, Li, Ca, Mg, Ag or Zn.

Synthesis of Riluzole Prodrugs

In one aspect, the riluzole prodrugs may be synthesized via intermediate form.

In one embodiment, the riluzole may be activated to produce an intermediate by reaction with methyl carboxyl group in basic condition.

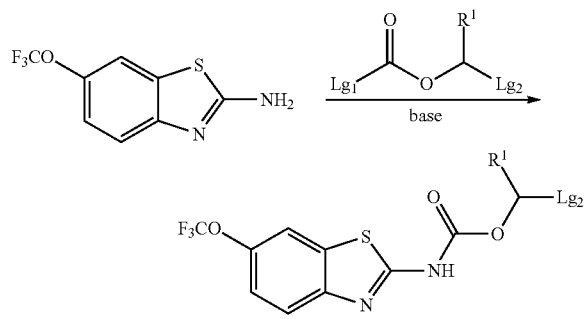

The intermediate may include a good leaving group, such as halide, and may be susceptible to a nucleophilic attack from other nucleophiles. Exemplary leaving group may be, but not limited to, Cl, Br, or I.

Exemplary reaction may be described as follows:

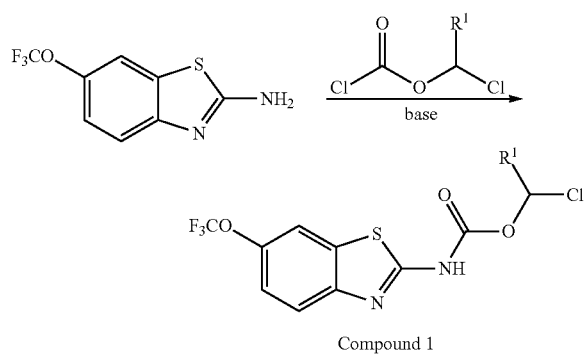

In one exemplary embodiment, the riluzole prodrug may be formed by Scheme 1 below. In Scheme 1, Compound 1 is reacted with carboxylate metal to produce Compound 2.

Scheme 1

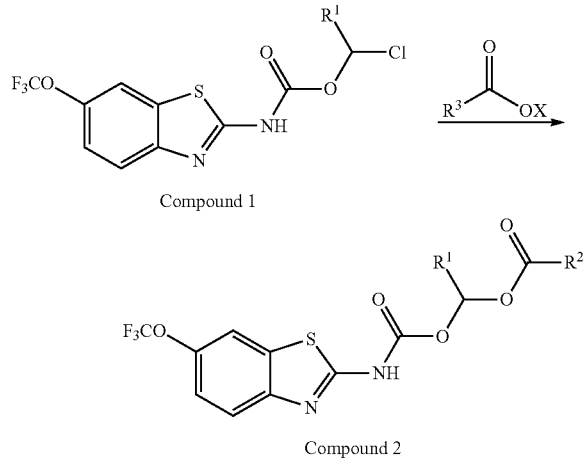

where $R^1$ is H, alkyl or particularly $C_1$-$C_8$ alkyl; $R^2$ is alkyl, cycloalkyl, aryl, or heteroaryl, or halo alkyl, which may be substituted or unsubstituted; and X is Na, K, Li, Ag or Zn. Further, the metal is Na, K, Li, Ca, Mg, Ag or Zn.

In one exemplary embodiment, the riluzole prodrug may be formed by Scheme 2 below. In Scheme 2, Compound 1 is reacted with phenyl carboxylate under basic condition to produce Compound 3.

Scheme 2

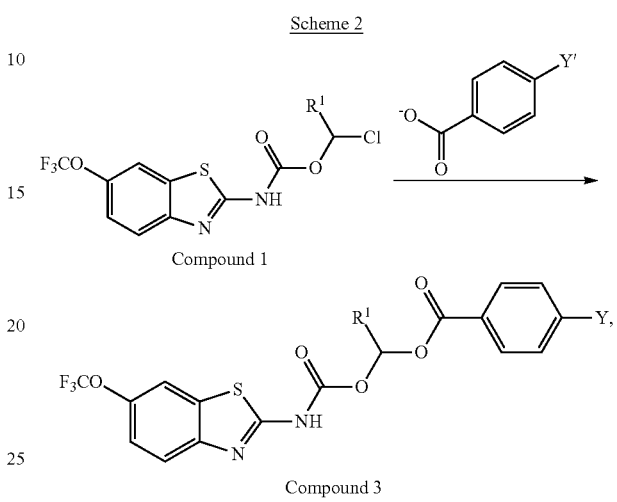

where $R^1$ is H, alkyl or particularly $C_1$-$C_8$ alkyl; Y is $PO_3H$, $CH_2PO_3H$ or salts thereof; and Y' is H, $PO_3Bc_2$, $CH_2PO_2Bc$, $MPO_3Bc$ or salt thereof, or $N(R_a)_4^+$, where Ra is H or alkyl.

In one exemplary embodiment, the riluzole prodrug may be formed by Scheme 3 below. In Scheme 3, Compound 1 is reacted with protected phosphate and the resulting compound is deprotected to produce Compound 3.

Scheme 3

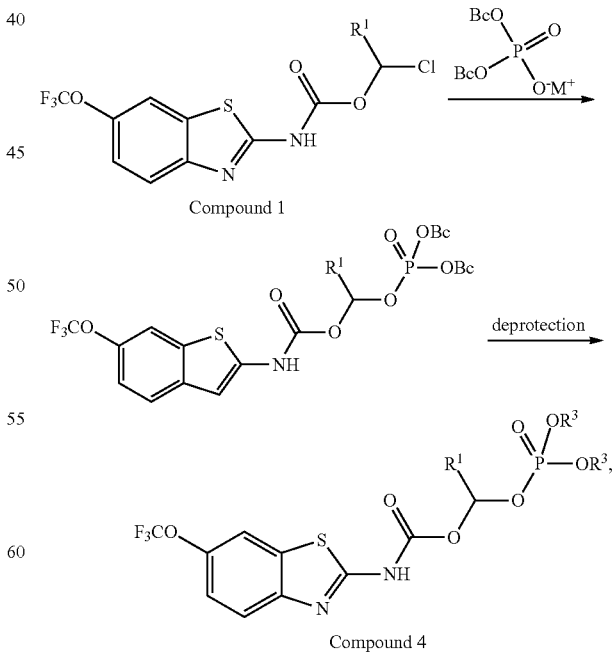

where $R^1$ is H, alkyl or particularly $C_1$-$C_8$ alkyl; $R^2$ is alkyl, cycloalkyl, aryl, or heteroaryl, or halo alkyl, which may be substituted or unsubstituted; $R^3$ is H, metal, $R^2$ or a substituted or unsubstituted primary, secondary or tertiary amine; and Bc is a protecting group. M is a metal including Na, K, Li, Ca, Mg, Ag or Zn.

In one exemplary embodiment, the riluzole prodrug may be formed by Scheme 4 and Scheme 4' below. In Scheme 4, Compound 1 is reacted with fumarate to produce Compound 5

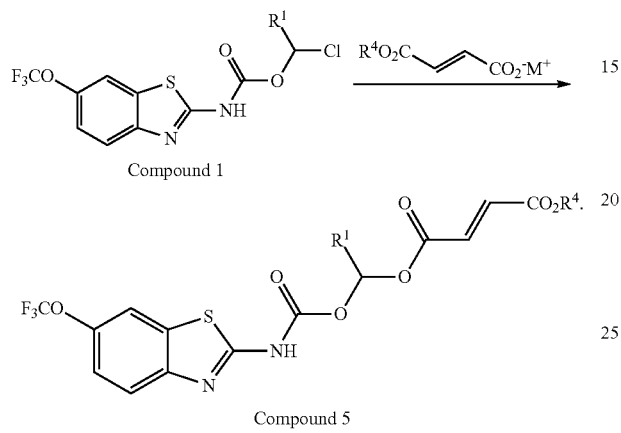

In Scheme 4', Compound 1 is reacted with a saturate, unsaturated, or conjugated dicarboxylic acid to produce Compound 5'.

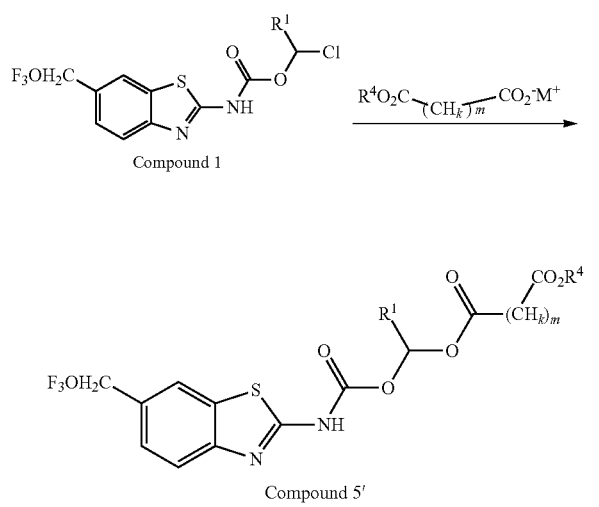

In Schemes 4 and 4', $R^1$ is H, alkyl or particularly $C_1$-$C_8$ alkyl; $R^4$ is H, metal, ammonium salt, or alkyl; k is 1 or 2, m is 2-22, or $(CH_k)_m$ is saturated, unsaturated or conjugated hydrocarbon; and M is a metal including Na, K, Li, Mg, Ca, Ag or Zn.

In one exemplary embodiment, the riluzole prodrug may be formed by Scheme 5 below. In Scheme 5, Compound 1 is reacted with protected aminoacetate and the resulting compound is deprotected to produce Compound 6.

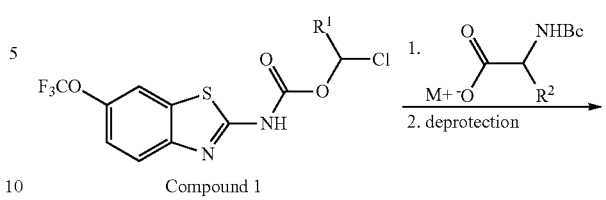

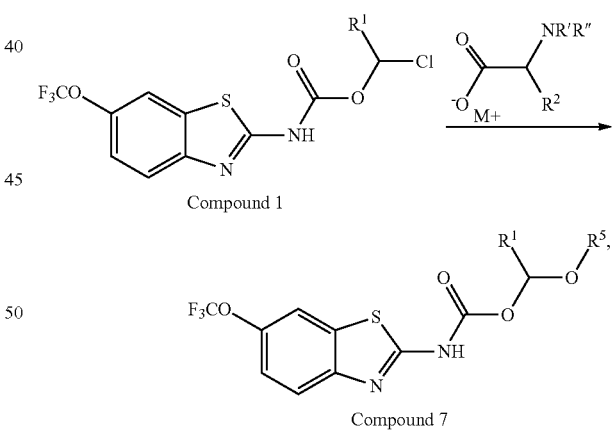

where $R^1$ is H, alkyl or particularly $C_1$-$C_8$ alkyl; $R^2$ is alkyl, cycloalkyl, aryl, or heteroaryl, or halo alkyl, which may be substituted or unsubstituted; and $R^5$ is a substituted or unsubstituted natural amino acid; and M is a metal including Na, K, Li, Mg, Ca, Ag or Zn. Bc is a protecting group.

In one exemplary embodiment, the riluzole prodrug may be formed by Scheme 6 below. In Scheme 6, Compound 1 is reacted with aminoacetate to produce Compound 7.

where $R^1$ is H, alkyl or particularly $C_1$-$C_8$ alkyl; and $R^5$ is a substituted or unsubstituted natural amino acid; and X is Na, K, Li, Ag or Zn.

In another embodiment, the riluzole prodrug may be formed using cesium carbonate for carbamination of amine efficiently.

In one exemplary embodiment, the riluzole prodrug may be formed in N-acyloxy carbamate form. In Scheme 7, activated carboxylic acid and carbon dioxide are condensed with riluzole to form the prodrug (compound 8).

Scheme 7

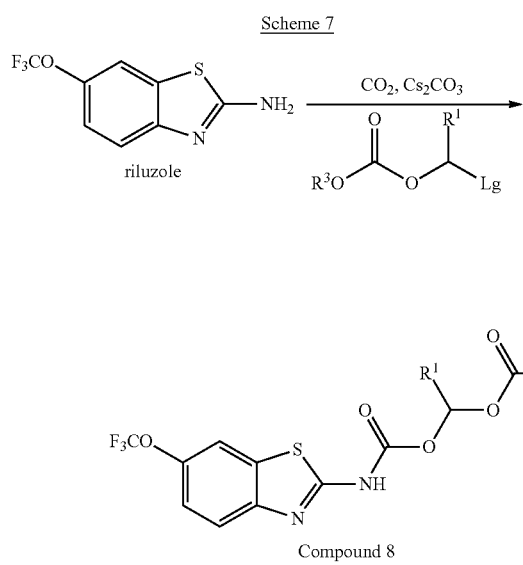

Compound 8 where R¹ is H, alkyl or particularly $C_1$-$C_8$ alkyl; Lg is a leaving group; R² is alkyl, cycloalkyl, aryl, or heteroaryl, or halo alkyl, which may be substituted or unsubstituted. In particular, Lg may be a halide, such as F, Cl, Br and I.

In Scheme 8, riluzole is reacted with 4-methyl 1,3-dioxol-2 one to produce Compound 9. In an exemplary embodiment, the prodrug may be synthesized as follows.

Scheme 8

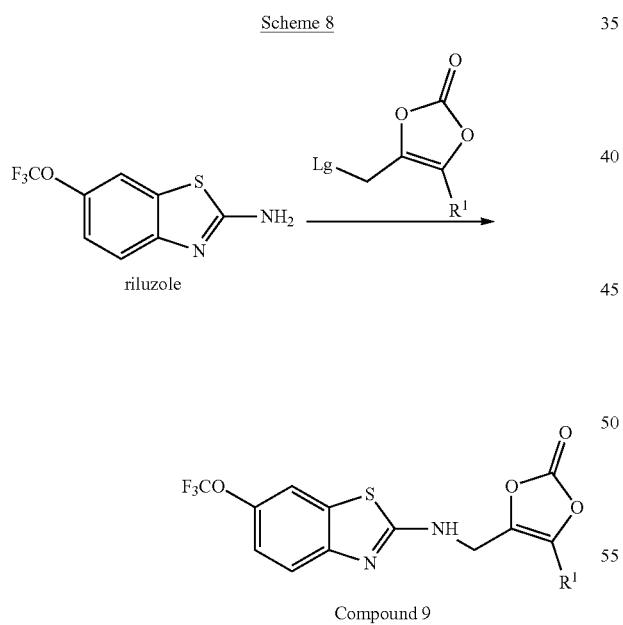

Compound 9 where R¹ is H, alkyl or particularly $C_1$-$C_8$ alkyl; Lg is a leaving group Lg is a leaving group. Particularly, Lg may be a halide, such as F, Cl, Br and I.

In Scheme 9, riluzole is reacted with isobenzofurane-1-one to produce Compound 10.

In an exemplary embodiment, the prodrug may be synthesized as follows.

Scheme 9

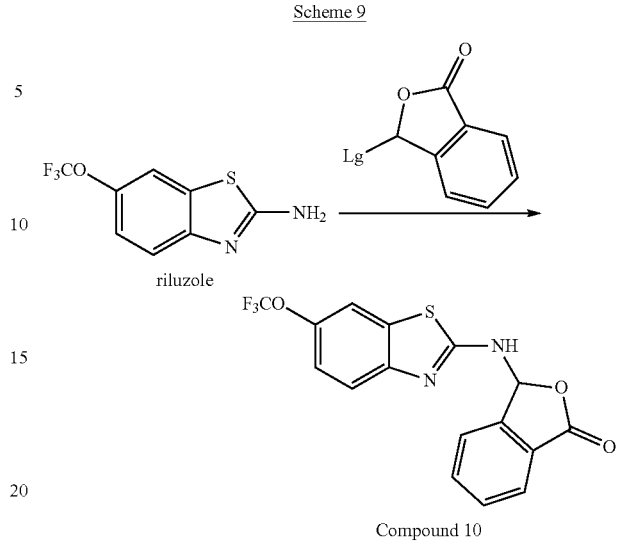

Compound 10

In particular, Lg is a leaving group. Lg may be a halide, such as F, Cl, Br and I.

In Scheme 10, riluzole is reacted with $((PhCH_2O)_2PO)_2O$ and sodium bis(trimethylsilyl)amide (NaHMDS) and the resulting compound is reacted with hydrogen gas to produce compound 11.

In an exemplary embodiment, the prodrug may be synthesized as follows:

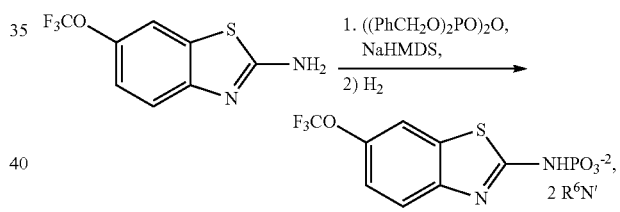

where R⁶ is alkyl, cycloalkyl, aryl, or heteroaryl, or halo alkyl; and N' isa primary, secondary and tertiary amine which is substituted or unsubstituted, or metal salts.

In one exemplary embodiment, N-acyloxy carbamate prodrug may also be synthesized using

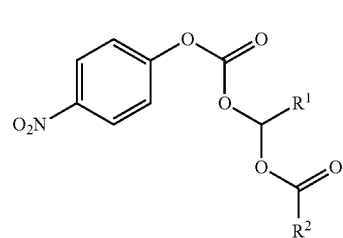

((4-nitrophenoxy)carbonyloxy)methyl formate, where R¹ is H, alkyl or particularly $C_1$-$C_8$ alkyl; and R² is alkyl, cycloalkyl, aryl, or heteroaryl, or halo alkyl, which is substituted or unsubstituted. Exemplary reaction scheme is shown as follows. In Scheme 11, riluzole is reacted with ((4-nitrophenoxy)carbonyloxy)methyl formate to produce Compound 12.

Scheme 11

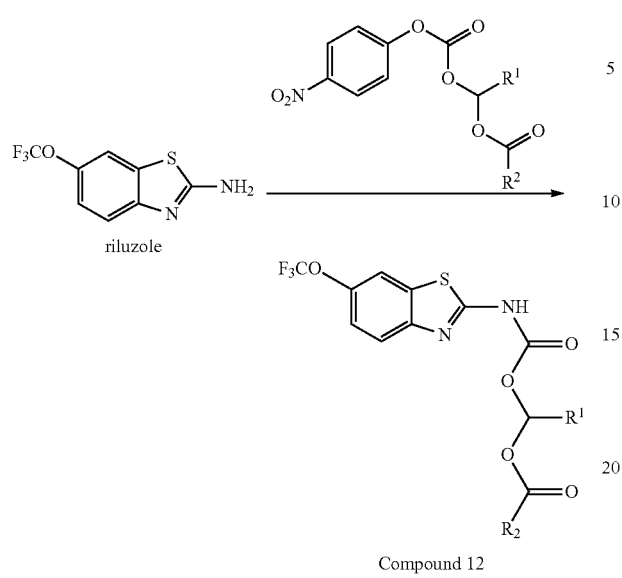

Compound 12

The entire contents of all patents, published patent applications and other references cited herein are hereby expressly incorporated herein in their entireties by reference.

Those skilled in the art will recognize, or be able to ascertain using no more than routine experimentation, numerous equivalents to the specific procedures described herein. Such equivalents are considered to be within the scope of this invention and are covered by the following claims.

I claim:

1. A prodrug consisting of a drug molecule and at least one or more prodrug appendage moieties, the prodrug is formed as:

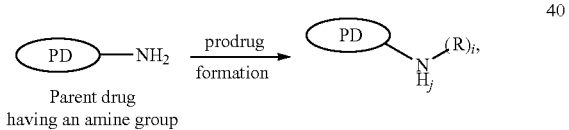

wherein the drug molecule is riluzole, and
wherein R is a prodrug appendage moiety, wherein the prodrug appendage moiety is coupled to amine of the drug molecule and is independently selected from the group of consisting of:

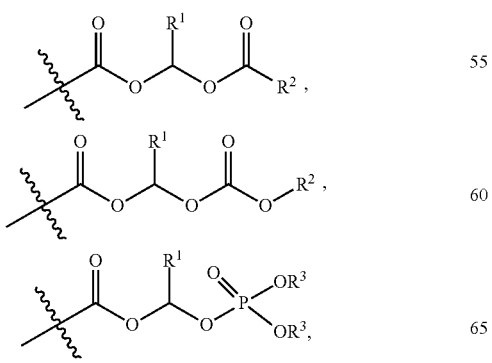

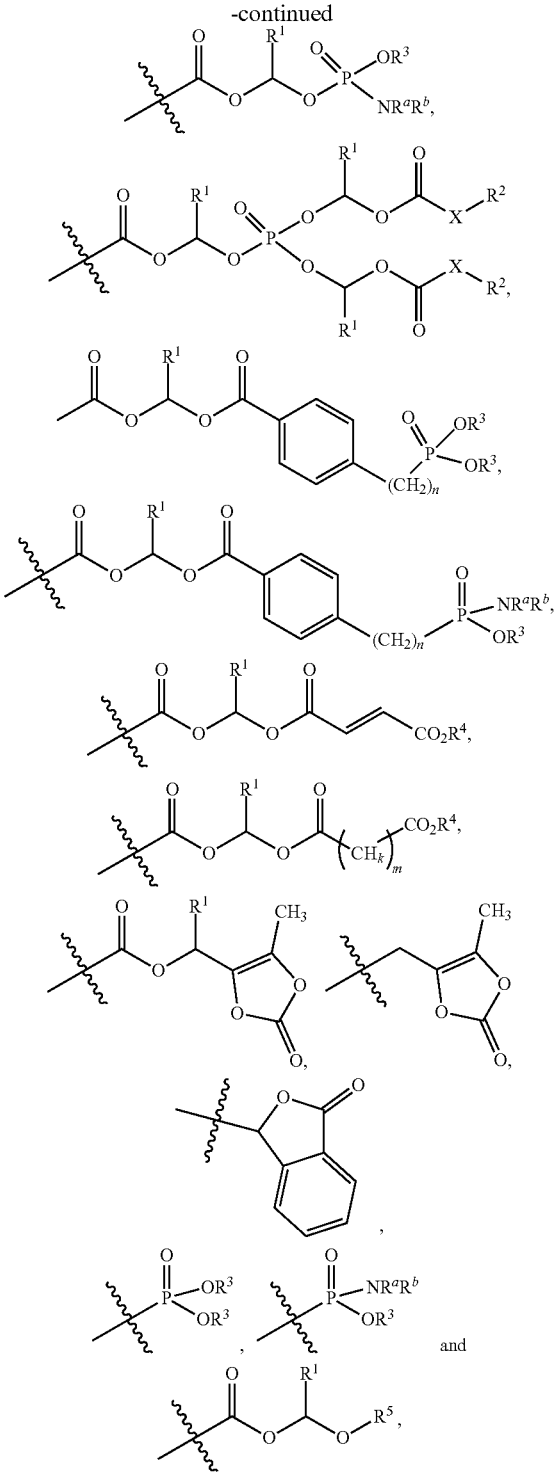

where $R^1$ is H or alkyl;
$R^2$ is alkyl, cycloalkyl, aryl, or heteroaryl, or halo alkyl, which is substituted or unsubstituted,
$R^3$ is H, metal, $R^2$ or a substituted or unsubstituted primary, secondary or tertiary amine;
$R^4$ is H, metal, ammonium salt or alkyl;
$R^5$ is a substituted or unsubstituted natural amino acid;
$R^a$ or $R^b$ is H, alkyl or aryl; or $NR^a$ or $NR^b$ is an amino acid;
X is $CH_2$ or O;

k is 1 or 2, m is 2-22, or $(CH_k)_m$ is saturated, unsaturated or conjugated hydrocarbon;

n is 0-2;

the metal is Na, K, Li, Ca, Mg, Ag or Zn, and wherein i is 1 or 2 and j is 0 or 1, wherein "substituted" refers to one or more substituents, which are the same or different, each replacing a hydrogen atom, wherein the one or more substituents are selected from the group consisting of F, Cl, Br, I, hydroxyl, amino, alkylamino, arylamino, dialkylamino, diarylamino, cyano, nitro, mercapto, oxo, thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, and cyclyl, wherein alkyl, alkenyl, alkyloxy, aryl, heteroaryl, and cyclyl are optionally substituted with alkyl, aryl, heteroaryl, halogen, hydroxyl, amino, mercapto, cyano, nitro, oxo, thioxo, or imino.

2. The prodrug of claim 1, wherein i is 1 and j is 1.

3. The prodrug of claim 1, wherein i is 2 and j is 0.

4. A prodrug of riluzole having a structure selected from:

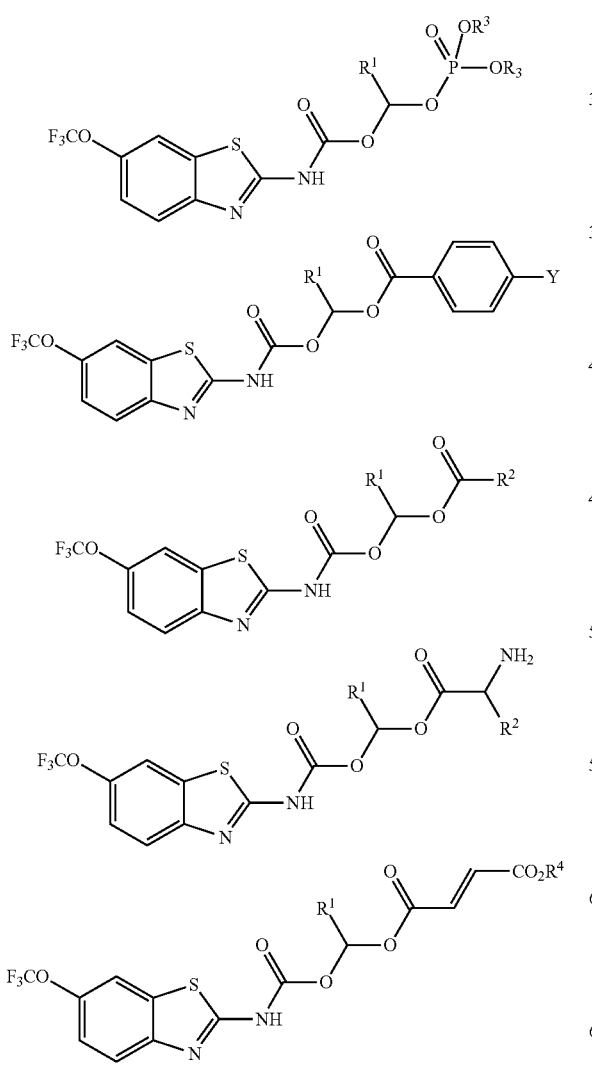

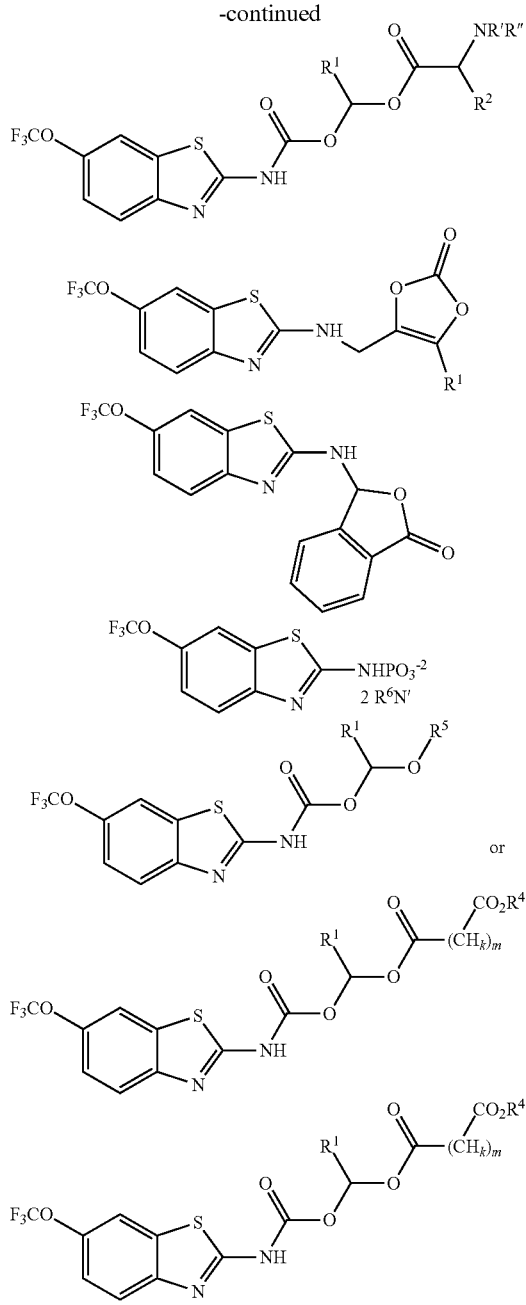

where $R^1$ is H or alkyl;
$R^2$ is alkyl, cycloalkyl, aryl, or heteroaryl, or halo alkyl, which is substituted or unsubstituted;
$R^3$ is H, metal, $R^2$ or a substituted or unsubstituted primary, secondary or tertiary amine;
$R^4$ is H, metal, ammonium salt or alkyl;
$R^5$ is a substituted or unsubstituted natural amino acid;
$R^6$ is alkyl, cycloalkyl, aryl, or heteroaryl, or halo alkyl;
R' and R" are cyclic or acyclic alkyl;
k is 1 or 2, m is 2-22, or $(CH_k)_m$ is saturated, unsaturated or conjugated hydrocarbon;
N' is a primary, secondary and tertiary amine which is substituted or unsubstituted, or metal salts;
Y is $PO_3H$, $CH_2PO_3H$ or salt thereof; and
the metal is Na, K, Li, Ca, Mg, Ag or Zn,
wherein "substituted" refers to one or more substituents, which are the same or different, each replacing a hydrogen atom, wherein the one or more substituents are selected from the group consisting of F, Cl, Br, I, hydroxyl, amino, alkylamino, arylamino, dialkylamino, diarylamino, cyano, nitro, mercapto, oxo, thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, and cyclyl, wherein alkyl, alkenyl, alkyloxy, aryl, heteroaryl, and cyclyl are optionally substituted with alkyl, aryl, heteroaryl, halogen, hydroxyl, amino, mercapto, cyano, nitro, oxo, thioxo, or imino.

* * * * *